United States Patent [19]

Cohenford

[11] Patent Number: 4,767,702
[45] Date of Patent: Aug. 30, 1988

[54] PAPER STRIP ASSAY FOR NEISSERIA SPECIES

[76] Inventor: Menashi A. Cohenford, 1 Cold Spring Dr., W. Warwick, R.I. 02893

[21] Appl. No.: 826,546

[22] Filed: Feb. 6, 1986

[51] Int. Cl.$^4$ ............................................. C12Q 1/36
[52] U.S. Cl. ........................................ 435/24; 435/18; 435/19; 435/23; 435/25; 435/29; 435/34; 435/805; 435/810; 422/56; 436/511
[58] Field of Search .................. 435/14, 24, 810, 805; 422/56; 436/511

[56] References Cited

U.S. PATENT DOCUMENTS

| | | | |
|---|---|---|---|
| 3,819,490 | 6/1974 | Klingstrom et al. | 435/805 |
| 4,654,310 | 3/1987 | Ly | 435/805 |
| 4,683,209 | 7/1987 | Ismail et al. | 435/14 |

OTHER PUBLICATIONS

D'Amato et al., J. Clin. Microbiol., 7, 77–81 (1978).
Janda et al., J. Clin. Microbiol., 21, 734–737 (1985).
Philip et al., J. Clin. Microbiol., 22, 101–104 (1985).
Welbourn et al., J. Clin. Microbiol., 20, 680–683 (1984).
Yajko et al., J. Clin. Microbiol., 19, 380–383 (1984).
Doyle et al., J. Clin. Microbiol., 3, 383–387 (1984).
Faur et al., J. Clin. Microbiol., 1, 294–297 (1975).

Primary Examiner—Sam Rosen
Attorney, Agent, or Firm—Ernest V. Linek; Donald Brown

[57] ABSTRACT

The present invention is directed to a rapid enzymatic method using chromogenic substrates for the identification of *Neisseria gonorrhoeae*, *Neisseria meningitidis* and *Neisseria lactamica*. The assay correlated 100% in its identification of pathogenic Neisseria with modified NYC fermentation medium. The assay is more sensitive in its direction of prolylaminopeptidase activity in *Neisseria meningitidis* than any of the commercially available systems.

The test method of the present invention is performed by first applying a small amount of buffer, then applying colonial growth, to each of three test areas (PAP, GAP, and BDG) on filter paper test strips. The strips are then incubated at from about 35°–37° for 10 minutes or at room temperature for 20 minutes. If the BDG area is positive (blue-green color) the isolate is identified as *Neisseria lactamica*. If the BDG area is negative, a chromogenic reagent, such as dimethylaminocinnaminaldehyde, is added to the PAP and GAP test areas. If a purple color develops in area B. *N. meningitidis* is present; however, if a red color develops solely in area C the presence of *Neisseria gonorrhoeae* is indicated.

13 Claims, 1 Drawing Sheet

PAPER STRIP ASSAY FOR NEISSERIA SPECIES

FIELD OF THE INVENTION

The present invention is directed to an assay product and method useful in the identification of gram negative diplococci from primary selective media growth. Such organisms include the pathogenic species of the genus Neisseria, e.g., *N. gonorrhoeae, N. meningitidis,* and *N. lactamica.* The present invention utilizes an absorbent solid support e.g., filter paper, to which has been added a chromogenic enzyme substrate. A test organisms reaction to this substrate is indicated by a color reaction after the addition of a specific reagent. This substrate reacts in the presence of the test organism by a color reaction.

BACKGROUND OF THE INVENTION

Bacteria of the genus Neisseria are responsible for causing two relatively common human diseases. *Neisseria gonorrhoeae* is the causative agent for gonorrhea and *Neisseria meningitidis* is the pathogen for one type of bacterial meningitis. Obviously, it is important for laboratories and physicians to be able to identify these bacteria quickly and accurately.

The use of chromogenic substrates to detect preformed enzymes for the identification of pathogenic Neisseria species was first described by D'Amato et al., *J. Clin. Microbiol.,* 7, 77–81 (1978).

Commercial products utilizing enzymatic substrates have generally been known to be simple, accurate, and relatively rapid. See for example, Janda, et al., *J. Clin. Microbiol.,* 21, 734–737 (1985); Philip et al., *J. Clin. Microbiol.,* 22, 101–104 (1985) and Welborn, et al., *J. Clin. Microbiol.,* 20, 680–683 (1984).

Most of these systems rely on the solution phase detection of three preformed enzymes, prolylamino peptidase (PAP), gamma-glutamylaminopeptidase (GAP), and Beta-D-galactosidase (BDG), which are associated with *Neisseria gonorrhoeae, Neisseria meningitidis,* and *Neisseria lactamica,* respectively.

It has also been reported that the solution phase detection of these enzymes approaches 100% specificity for each of the three Neisseria species. See, D'Amato, et al., supra; Yajko, et al., *J. Clin. Microbiol.,* 19, 380–383 (1984); Janda, et al., supra; Philip et al., supra; and Welborn, et al., supra.

One commercially available test for the identification of Neisseria species from isolation media is Gonochek II® (E. I. Du Pont de Nemours & Co., Wilmington, DE 19898). The Gonochek II test utilizes three chromogenic substrates contained in a single tube to detect preformed enzymes associated with the three Neisseria species.

Suspect organisms from suitable selective media are transferred to the Gonochek tube and incubated for 30 minutes at 35° C. After the addition of reagent, color reactions reveal specific enzymes in the solution. These enzymes are confirmatory for three Neisseria species; prolylaminopeptidase for *N. gonorrhoeae,* gamma-glutamylaminopeptidase for *N. meningitidis,* and beta-d-galactosidase for *N. lactamica.*

When an isolate is removed from selective media, detection of PAP alone identifies *Neisseria gonorrhoeae,* GAP identifies *Neisseria meningitidis,* and BDG identifies *Neisseria lactamica.* However, exceptions have been noted. For example, using the Gonocheck II system, Philip et al., supra, found that 4.6% of the *Neisseria meningitidis* strains were negative for GAP, while Janda et al., supra, found 5 of 172 (3%) of the *Neisseria meningitidis* isolates negative for GAP. PAP positive *Neisseria meningitidis* isolates have also been reported by Yajko et al., supra, who found 43% positive and by D'Amato et al., supra, who reported 6.7% positive.

The present invention is directed to a system (i.e., both a product and process) designed to identify these same enzymes from Neisseria species on a solid absorbent, e.g., filter paper, rather than in solution.

The preferred test strip of the present invention comprises three sections of filter paper each impregnated with one of the three Neisseria species specific substrates. After the addition of a buffer, the suspect organism is smeared on each filter paper section, and the strip is incubated at 35° C. for 10 minutes at 35°–37° C. or 20 minutes at room temperature. If no color develops in section A after the incubation period, a color developing reagent is added to produce a color reaction on selected sections.

In comparison to the solution phase assay methods of the prior art, the assay test of the present invention has been found to be:

1. more rapid (immediate color formation after incubation)
2. more sensitive (intense color formation)
3. less subjective (clear results +/−)
4. more convenient (no messy tubes, etc.)

There is no other commercially available direct enzymatic test system designed to detect all three Neisseria species on filter paper. Additionally, although the color reagent preferably employed (dimethylaminocinnaminaldehyde) has been previously used in solution by microbiologists (the API system is one example), never before has it been adapted for use in a commercial test on filter paper for the rapid identification of bacterial polyaminopeptidase and gamma-glutamy/aminopeptidase.

SUMMARY OF THE INVENTION

The present invention is directed to a new product for the identification of pathogenic Neisseria species. This product comprises an absorbent solid support, preferably a filter paper strip, said support containing the Neisseria enzyme substrates. A kit for using the test strip of the present invention would also include a buffer, and a chromogenic reagent.

The test method of the present invention is performed by applying isolated colonial growth to each of three test areas after the addition of buffer (A, i.e., BDG, B, i.e., GAP, and C, i.e., PAP) on the filter paper strip. The strip is then incubated at about 35°–37° C. for 10 minutes or room temperature for 20 minutes. If the BDG area is positive (blue-green color) the isolate is identified as *Neisseria lactamica.* If the BDG area is negative, a chromogenic reagent is then added to the PAP and GAP test areas. Depending upon where the color development occurs, the identification of *Neisseria meningitidis* (positive GAP) or *Neisseria gonorrhoea* (positive PAP)

is continued. If none of the test areas show a positive reaction, the isolate may presumptively be identified as *Branhamella catarrhalis*.

DETAILED DESCRIPTION OF THE PREFERRED EMBODIMENTS

The present invention is directed to a test system for the rapid identification of pathogenic Neisseria from plated media growth and to the method of using that system. The system utilizes three chromogenic substrates, preferably impregnated on filter paper, to detect the preformed enzymes associated with *Neisseria gonorrhoeae, Neisseria meningitidis*, and *Neisseria lactamica*.

Figure 1:
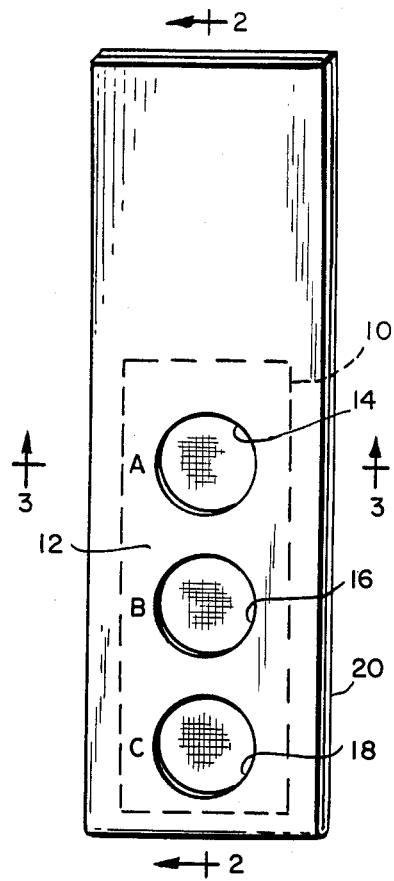
FIG. 1 is a plan view of one possible configuration of the filter paper test strip of the present invention.
Figure 2:
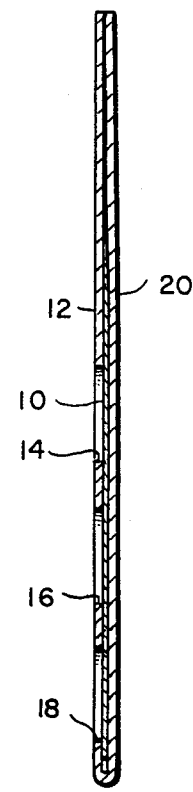
FIG. 2 is a side view of the filter paper test strip of FIG. 1 taken along section line 2—2.
Figure 3:
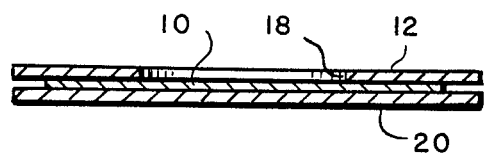
FIG. 3 is an end view of the filter paper test strip of FIG. 1 taken along section line 3—3.

Referring to the Figures, there are depicted in FIGS. 1, 2 and 3, three views of one preferred arrangement for the test strip of the present invention.

As illustrated, the preferred test strip comprises a section of filter paper 10 and a separator 12. The separator 12 has three openings 14, 16, and 18, exposing the filter paper 10. Beneath filter paper 10 is a backing 20, which supports the filter paper. Openings 14, 16 and 18 serve as the test areas and are each individually treated with an effective amount of an enzyme substrate specific for *Neisseria lactamica* (e.g., 5-bromo-4-chloro-3-indolyl-beta-d-galactopyranoside, for BDG), *Neisseria meningitidis* (e.g., 1-gamma-glutamyl-p-nitroanalide hydrochloride, for GAP), and *Neisseria gonorrhoeae* (e.g., 1-proline-beta-naphthylamide hydrochloride, for PAP). The separator 12 prevents interaction among the three test areas.

Suspect colonies are taken from suitable selective media (e.g., Modified Thayer Martin agar) with a wooden applicator stick, swab or inoculating needle and smeared on the three test areas of the filter paper test strip. With 10-20 minutes the test strip is read for the detection of the enzymes produced by Neisseria as described for example by Yajko et al., supra; D'Amato et al., supra; and Doyle et al., *J. Clin. Microbiol.*, 3, 383-387 (1984).

Evaluations of 13 strains of *Neisseria gonorrhoeae*, 10 strains of *Neisseria meningitidis*, 4 strains of *Neisseria lactamica*, and 1 strain of *Branhamella catarrhalis* indicated that the product and method of the present invention correlated 100% with modified NYC fermentation medium. See for example, Faur, et al., *J. Clin. Microbiol.*, 1, 294-297 (1975).

All 13/13 isolates of *Neisseria gonorrhoeae* were positive for PAP and negative for GAP and BDG. All 10/10 isolates of *Neisseria meningitidis* proved positive for GAP and PAP.

The incidence in detection of PAP was found to be much higher in *Neisseria meningitidis* than in the previously reported solution systems, e.g., Gonocheck II, (see, D'Amato, et al., supra, and Yajko, et al., supra). It is believed that this increased percentage of PAP detection is due to the greater sensitivity of the filter paper methodology of the present invention. Based on the above observations, it is also recommended that *Neisseria meningitidis* be designated as PAP positive.

The present invention is also directed to a kit for conducting the assay of the the present invention. Each kit would contain reagents sufficient to perform one or more (e.g., 25) tests and would include for example:
Reagent #1: Buffer (e.g., 0.1M potassium phosphate)
Reagent 190 2: Color developer (e.g., dimethylaminocinnaminaldehyde)
test strips having three pretreated spots:
Area A: Beta-D-Galactosidase (BDG)
Area B: Gamma-glutamylaminopeptidase (GAP) substrate
Area C: Prolylaminopeptidase (PAP) substrate The kits would necessarily be stored at from about 2° to 8° C. until use and then brought to room temperature just prior to use.

The innoculum should be from an 18-24 hour growth on selective media (e.g., Modified Thayer Martin agar) or chocolate agar if subcultured from selective media. The organism should first be presumptively identified as belonging to the genus Neisseria by the gram stain and oxidase test.

In general, the method of the present invention may be described as follows (see FIG. 1):

Add 3-4 drops of Reagent #1 (Buffer) to each test area, using a wooden stick, swab, or inoculating needle smear 1-2 colonies on each of the three filter paper strip test areas (A, i.e., BDG; B, i.e., GAP; and C, i.e., PAP).

Incubate the entire strip, preferably at 35° C. to 37° C. for about 10 minutes or at room temperature for 20 minutes.

If the innoculum on area A (the BDG test) has turned blue-green, the isolate has been identified as *Neisseria lactamica* and no further manipulations are necessary.

If the area A is negative (i.e., no blue-green color development) add 2 drops of Reagent #2 (color developer) to test areas B and C (PAP and GAP). A positive reaction in these test areas is denoted by a purple color in area B and/or red color in area C within about 60 seconds immediately surrounding the innoculum.

The present invention is based upon the colors produced by the enzyme—substrate interactions of the three Neisseria species. While this principle has previously been applied in a solution phase assay, the use of an absorbent solid support has been found to unexpectedly enhance both the speed and the sensitivity of the reactions. Prolylaminopeptidase (PAP) is an enzyme produced by *Neisseria gonorrhoeae*. Gamma-glutamyl aminopeptidase (GAP) is an enzyme produced by *Neisseria meningitidis*. The majority of *N. meningitidis* isolates will react positively for PAP, however *N. gonorrhoeae* will not react positively for GAP. Beta-D-galactosidase (BDG) is an enzyme produced by *Neisseria lactamica*, any positive BDG test identifies the isolate as *Neisseria lactamica*.

These reactions are summarized in the following Table:

EXPECTED RESULTS

|  | C PAP | B GAP | A BDG |
|---|---|---|---|
| *Neisseria gonorrhoeae* | + | − | − |
| *Neisseria meningitidis* | +/− | + | − |
| *Neisseria lactamica* | +/− | +/− | + |
| *Branhamella catarrhalis* (presumptive) | − | − | − |

If PAP, GAP, and BDG are all negative, the isolate may be presumptively identified as *Branhamella catarrhalis*. Further testing should be performed to confirm this identification.

Quality control should be performed in accordance with standard laboratory practice using organisms that will produce known positive and negative reactions. The following American Type Culture Collection strains are recommended:

| | |
|---|---|
| *N. gonorrhoeae* | ATCC 19424 |
| *N. meningitidis* | ATCC 23970 |
| *N. lactamica* | ATCC 13077 |
| *B. catarrhalis* | ATCC 25238 |

The test product of the present invention is intended for the identification of oxidase positive, gram negative diplococci from primary selective media growth. It is not intended for use with a primary media non-selective agar such as chocolate agar since other Neisseria species (e.g., *N. sicca, N. mucosa,* etc.) may grow.

Other Neisseria species may likewise appear on selective media after prolonged incubation (36-48 hours). If the presence of such other Neisseria species is suspected, subculture to a nutrient agar as *N. gonorrhoeae* and *N. meningitidis* will not grow at 35° C. in room air.

The test strip of the present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1

The preferred test strip of FIG. 1 was constructed as follows:

Heavy paper stock (e.g., bristol board) was cut into a piece (3.5mm×25 mm) and folded lengthwise in half, providing an top member and a bottom member. Three holes (each 1.5 mm in diameter) were cut into the lower half of the top member. Hole C was spaced 0.5 mm from the folded end of the top member, hole B was spaced 0.05 mm from hole C and hole A was spaced 0.5 mm from hole B.

A section of filter paper (Schleicher & Schuell, Inc. No. 407C, 2.5 mm×8 mm) was placed between the folded top and bottom members against the fold such that filter paper was present in each hole when the top and bottom members were brought together. Adhesive was used to seal the top and bottom members, securing the filter paper section there between.

The enzyme substrates used are commercially available (e.g., Sigma Chemical Company). The three filter paper test areas (A, B, and C) were treated with substrates as follows:

Area A: 0.16 mg of 5-bromo-4-chloro-3-indolyl-beta-d-galactopyranoside (Sigma No. B4252)—substrate for BDG;

Area B: 0.4 mg of 1-gamma-glutamyl-p-nitro analide hydrochloride (Sigma No. G-6133)—substrate for GAP; and Area C: 0.8 mg of 1-proline-beta-naphthylamide hydrochloride (Sigma No. P1380)—substrate for PAP.

The phosphate buffer was prepared using reagent grade materials to afford 0.1M potassium phosphate buffer, pH 7.5, containing 0.5% Brij-35 (Sigma No. P1254) and 0.1% sodium azide.

The color reagent was prepared as follows; dimethyl aminocinnaminaldehyde (Sigma No. D4506, 0.25 g) was dissolved in 5 ml methanol and 5 ml conc. hydrochloric acid. This solution was diluted with 100 ml water. To this solution (110 ml) was added 40 ml of the potassium phosphate buffer (supra).

EXAMPLE 2

Twenty eight laboratory strains of pathogenic Neisseria were tested using the product and method of the present invention and modified NYC fermentation medium (see, Faur et al., supra).

Colonia growth of each pathogenic Neisseria strain were smeared on each of the three filter paper strip test areas (PAP, GAP, BDG). Buffer, four (4) drops, was added to each test area and the strip was incubated at 35°-37° C. for 10 minutes. The test strip was then removed from the incubator and examined in accord with the color profile described hereinabove.

For samples wherein the BDG area tested negative, the strip was treated with the color developer, dimethylaminocinnaminaldehyde. Again, the strip was examined as above.

The product and method of the present invention correctly identified 100% (28/28) of the isolates tested. The results are summarized in the following Table:

IDENTIFICATION OF PATHOGENIC NEISSERIA

| Organisms | # of Strains | # Correctly Identified (%) |
|---|---|---|
| *N. gonorrhoeae* | 13 | 13 (100) |
| *N. meningitidis* | 10 | 10 (100) |
| *N. lactamica* | 4 | 4 (100) |
| *B. catarrhalis* | 1 | 1 (100) |
| Total | 28 | 28 (100) |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

I claim:

1. An assay test strip comprising an absorbent solid support, said solid support bearing indicator means for the enzymes prolylamino peptidase (PAP), gamma-glutamylamino peptidase (GAP), and beta-D-galactosidase (BDG), said enzyme being produced by oxidase positive, Gram negative diplococci from primary selective media growth.

2. The assay test strip of claim 1, further comprising;
   (b) a separator having at least one opening for sample introduction, said separator contacting the top of said absorbent solid support.

3. The assay test strip of claim 2, further comprising;
   (c) a bottom member supporting said absorbent solid support.

4. The assay test strip of claim 3, wherein said absorbent solid support is a section of filter paper.

5. The assay test strip of claim 4, wherein the separator has three openings.

6. The method of assaying a suspect organism for the determination of its identity as *N. gonorrhoeae, N. meningitidis,* or *N. lactamica,* said method comprising the steps of:
   (a) smearing a test strip as defined in claim 1, with a sufficient quantity of the suspect organism;
   (b) adding a quantity of buffer and incubating the smeared test strip.

7. The assay test method of claim 6, further comprising;

(c) adding a color developing reagent to the incubated test strip; and (d) analyzing the test strip for colorogenic indications.

8. The assay test method of claim 7, wherein the color developing reagent is dimethylaminocinnaminaldehyde.

9. A filter paper assay test strip for the identification of Neisseria species selected from *N. gonorrhoeae*, *N. meningitidis*, and *N. lactamica*, said test strip comprising in combination:

(a) a filter paper strip;

(b) a separator attached to and effectively sealing one side of said filter paper strip, said separator being provided with three openings which expose said filter paper strip; and (c) a support member located on the remaining side of said filter paper strip, sealing said strip;

said filter paper exposed by the openings in said separator each containing an effective amount of one of the substrates specific for enzymes selected from the group consisting of prolylamino peptidase (PAP), gamma-glutamylamino peptidase (GAP), and beta-D-galactosidase (BDG), with the proviso that substrates for all three enzymes are represented on the filter paper strip.

10. The filter paper assay strip of claim 9, further comprising an effective quantity of buffer on each of the exposed openings.

11. The filter paper test strip of claim 10, further comprising an effective quantity of a color developing agent on the PAP and GAP openings.

12. A filter paper assay method for the identification of Nisseria species selected from *N. gonorrhoeae*, *N. memingitidis*, and *N. lactamica*, said test assay method comprising the steps of:

(a) smearing a sufficient quantity of a test innoculum on each of the filter paper openings in the test strip of claim 9;

(b) adding a quantity of potassium phosphate to each of the filter paper openings treated in step (a);

(c) incubating the test strip at about 35° C. for about 10 minutes;

(d) analyzing the BDG portion of the test strip.

13. The assay method of claim 10, further comprising:

(e) treating the PAP and GAP portions of the test strip with a sufficient quantity of dimethylaminocinnaminaldehyde;

(f) analyzing the PAP and GAP portions of the test strip.

* * * * *